United States Patent [19]

Motchenbacher et al.

[11] 4,337,658

[45] Jul. 6, 1982

[54] HUMIDITY SENSOR

[75] Inventors: Curtus D. Motchenbacher, Minnetonka; Merle E. Nicholas, Minneapolis, both of Minn.

[73] Assignee: Honeywell Inc., Minneapolis, Minn.

[21] Appl. No.: 301,697

[22] Filed: Sep. 14, 1981

Related U.S. Application Data

[63] Continuation-in-part of Ser. No. 196,902, Oct. 14, 1980, abandoned.

[51] Int. Cl.³ .............................................. G01W 1/00
[52] U.S. Cl. ...................................... 73/335; 29/620; 338/35
[58] Field of Search ...................... 73/336.5, 336, 335; 338/35, 34; 29/620

[56] References Cited

U.S. PATENT DOCUMENTS

| | | | |
|---|---|---|---|
| 3,671,913 | 6/1972 | Mamiya et al. | 73/336.5 |
| 4,143,177 | 3/1979 | Kovac et al. | 73/336.5 |
| 4,203,087 | 5/1980 | Kovac et al. | 73/336.5 |

Primary Examiner—Donald O. Woodiel
Attorney, Agent, or Firm—Omund R. Dahle

[57] ABSTRACT

A humidity sensor having an extended impedance range extending up to $10^{12}$ ohms precludes leakage currents. The sensor is in the form of an insulating substrate having conductive film such as gold applied to a surface thereof. The perimeter of a first film is completely encompassed by but spaced from a second film on the surface of the substrate. A humidity responsive layer of iron oxide is applied over the film layers to bridge the spacing therebetween in a continuous manner. Electrical terminals are connected, respectively, to the two films to provide a readout in terms of humidity.

22 Claims, 5 Drawing Figures

HUMIDITY SENSOR

This is a continuation-in-part of application Ser. No. 196,902, filed Oct. 14, 1980, now abandoned.

BACKGROUND AND SUMMARY OF THE INVENTION

The present invention relates to humidity or moisture sensing elements. The providing of suitable instruments for the measurement of relative humidity (RH) over wide ranges of RH (eg 10-90%) continues to be a challenging problem. While conventional humidity sensors have upper ohmic ranges of up to $10^6$ ohms a special electrode design and high impedance circuit in the present invention provide for routine measurement up to $10^{12}$ ohms. A conventional humidity measuring system is limited in the ability to measure values above $10^6$ ohms because of noise pickup. Our new design presents very little antenna effect because of the small surface of the sensor and all the leads are isolated. The nature of the present humidity sensor allows for the miniaturizing of the sensor without sacrificing lifetime and stability. Because the impedance is high, the electrical currents in the sensor are minute and the $I^2R$ heating effect is very low. The sensor can thus be reduced in size. The sensor might be described as one having an extended impedance range in that while the impedance at high humidities (i.e. 90% RH) is in the order of $10^3$ ohms (this being similar to existing RH sensors), the impedance at low humidities (i.e. 10% RH) is in the order of $10^{12}$ ohms with a $10^6$ impedance at about 35% RH. Thus the improved sensor extends the range into the higher impedances moving up from prior devices at about $10^6$ to about $10^{12}$ ohms. Thus when referring to a high impedance sensing element herein we mean that at the low range of relative humidity (under very dry conditions), the resistance from conductor 11 to conductor 12 through the iron oxide is in the order of $10^{12}$ ohms.

In the prior art it has been known to use iron oxide in a humidity sensitive element as has been described in the article "Electrical properties of iron oxide polyethylene glycol humidity sensitive elements" by Nicholas, Pitkanen, Lavine, Zook and Hagen, May 1976, Journal of Applied Physics, Vol. 47, No. 5 Pages 2191-2199. That disclosure, however, was directed to a much lower impedance device, the polyethylene glycol being combined with the $Fe_2O_3$ for the specific purpose of reducing the impedance.

When a high impedance device ($10^{12}$ ohms) of the nature of the present invention is desired there are special problems to be overcome, one of which problems is that of leakage currents. The novel design of the present detector is specifically directed to overcome this problem. Thus the described structure is easy to make and yet easy to control stray leakage paths. The low impedance guarded structure reduces pickup by providing shielding. The compact structure provides low electrical pickup in that the small geometry results in small capacity to radiating electric fields.

DESCRIPTION

A high impedance relative humidity sensing element is provided by applying onto an insulating substrate a conductive film such as gold, the perimeter of the first film being completely encompassed by but spaced from a second conductive film on the non-conducting substrate. A humidity responsive layer of iron oxide is applied over the conductive film layers and the spacing, to bridge the spacing in a continuous manner with the humidity responsive layer. Electrical terminals are connected, respectively, to the two conductive film layers.

Figure 1:
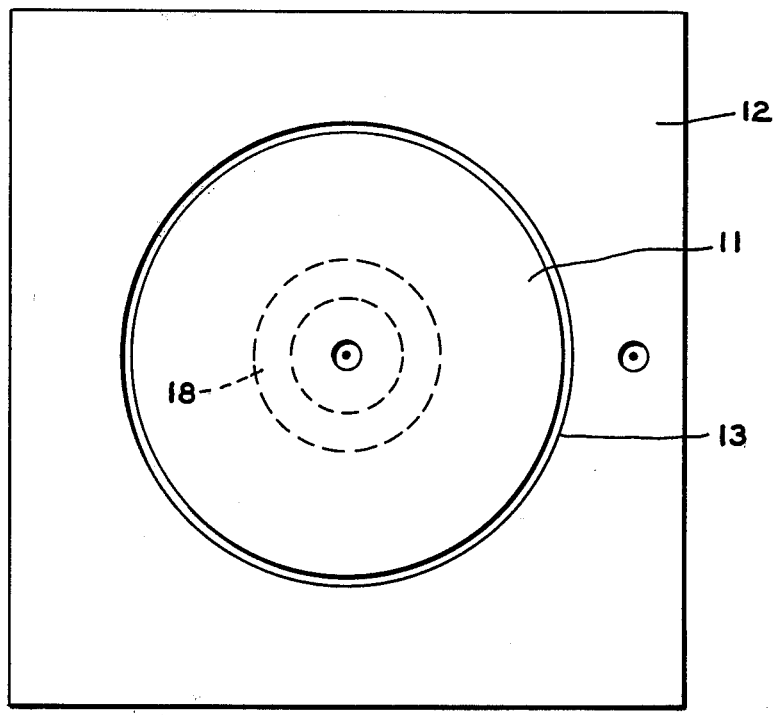
FIG. 1 is a top plan view of one embodiment of a high impedance humidity sensor according to the invention.
Figure 2:
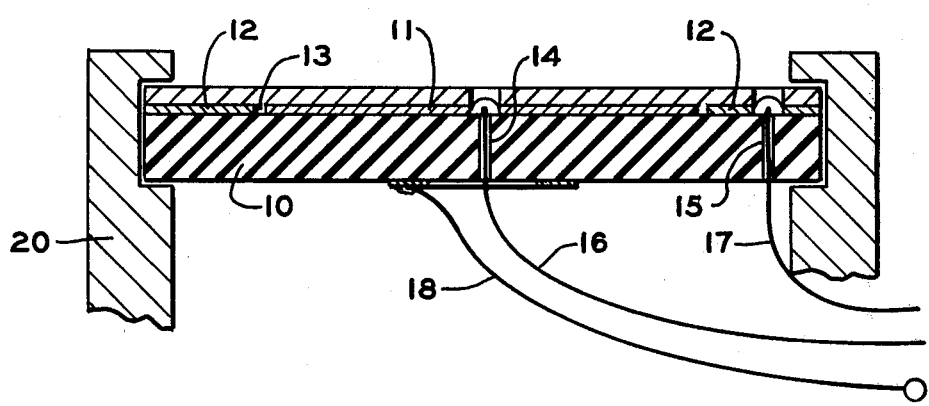
FIG. 2 is a cross sectional view of the sensor of FIG. 1 as well as of further sensor supporting structure.

Referring now to FIGS. 1 and 2 there is shown an insulating substrate 10, such as non-conducting high density high purity ceramic or glass. Examples are AlSiMag, alumina, sapphire and quartz. The substrate has applied on the upper surface thereof an inner conductive film 11, such as evaporated gold, and an outer conductive film 12, also evaporated gold. A spacing belt 13 of about 0.003" width, for example, may be used between the inner and encompassing films. In one successful embodiment the substrate used was 3 M 614 AlSi-Mag high-density high-purity 0.025" thick, cut into 1" squares. Two small holes 14 and 15 may be drilled through the substrate for bringing in the lead wires 16 and 17 from the back side if desired. One entire cleaned surface was coated with evaporated gold except for the 0.003" spacing belt. The gold may be applied by silk screening if desired. A firing process follows. The four edges were masked to about 1/16" onto the gold surface 12 as well as a circular area 1/16" in center on surface 11 and then the surface was uniformly coated with the humidity sensitive iron oxide. The iron oxide suspended in a dilute aqueous solution of polyvinyl alcohol was applied with an airbrush in one instance, until the applied oxide film was sufficiently opaque to obscure the gold of the electrode layers 11 and 12. This may require heaters to dry the oxide between sequentially applied layers. The iron oxide was then sintered at about 1080°-1100° C. for about 13-15 minutes to complete the sensor. During the sintering process the iron oxide powder interlocks to form porous balls and also attaches to the electrodes. Unsintered iron oxide sensors may also be used, if desired.

While the invention has been described in terms of the humidity sensor layer or film being of iron oxide ($Fe_2O_3$) as the preferred embodiment, the humidity sensitive layer material more generally may be selected from a hygroscopic metal oxide, a hygroscopic polymer (doped or untreated) or an inorganic salt. It is known that these materials, when in proper form, exhibit the high resistance of electrical insulators. It is known that certain of the oxides are hygroscopic in nature which affects their insulating properties such that when exposed to an atmosphere containing a quantity of water vapor, the value of electrical resistance changes as a function of the water vapor in the atmosphere. Desirable properties including humidity dependent resistances and a high degree of chemical stability are especially prevalent in the oxides of the metals of Group VIII, Period 4 of the Periodic Table of the Elements. Thus while others may be used, the oxides of iron, nickel and cobalt are preferred, in accordance with the present invention. As to the doped polymer an example of a suitable material is polyvinyl alcohol with lithium chloride. Suitable untreated polymers include polyethylene fluoride and polyimides. Suitable inorganic salts include lithium fluoride, lead iodide, cerium titanate and sodium hydrogen phosphate.

Figure 3:
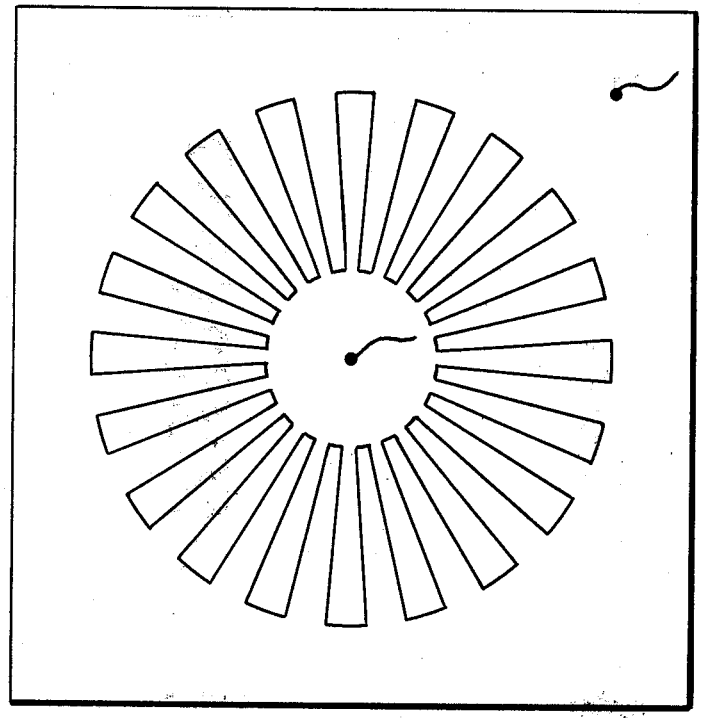
FIG. 3 is a modification of FIG. 1.
Figure 4:
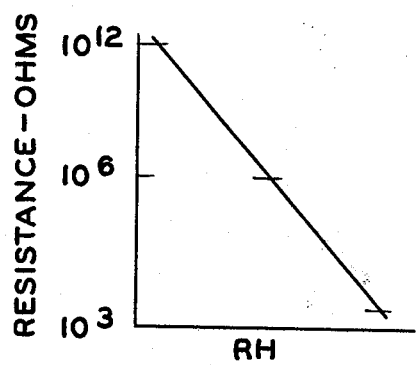
FIG. 4 is a graph of impedance vs. RH of the humidity sensor.

In the embodiment of FIGS. 1 and 2 the outer electrode 12 is shown as being concentric around the inner electrode 11 and the spacing 13 between the electrodes appears as a ring shape. While it is necessary that the spacing ring 13 close on itself and be continuous, it is not necessary that it describe a circle with a fixed radius. The spacing ring 13 may have a generally rectangular design or may be serpentine to increase the path length as shown in FIG. 3. In each case the iron oxide is applied over the spacing ring and the inner and outer conductive electrodes to bridge the spacing ring with iron oxide in a continuous manner. If the lead 16 is brought out through the back side as shown in FIGS. 1 and 2 then it is desirable to have a guard ring 18 on the back side of the substrate.

The technique of guarding is utilized in the present sensor structure. When designing with high impedance sensors, stray leakage paths caused by surface contamination result in errors in measurements. To avoid the requirement for maintaining clean uncontaminated surfaces in the operating environment it is often desirable to provide a terminating path for the leakage currents. One technique is called guarding. A guard ring provides a conductor shield around the sensor signal sense point. This guard ring is maintained at the signal electrical potential by means of electronic circuitry. Since there is no electric potential between the guard ring and the signal sense point, there is no stray conducted leakage signal to cause measurement error.

Figure 5:
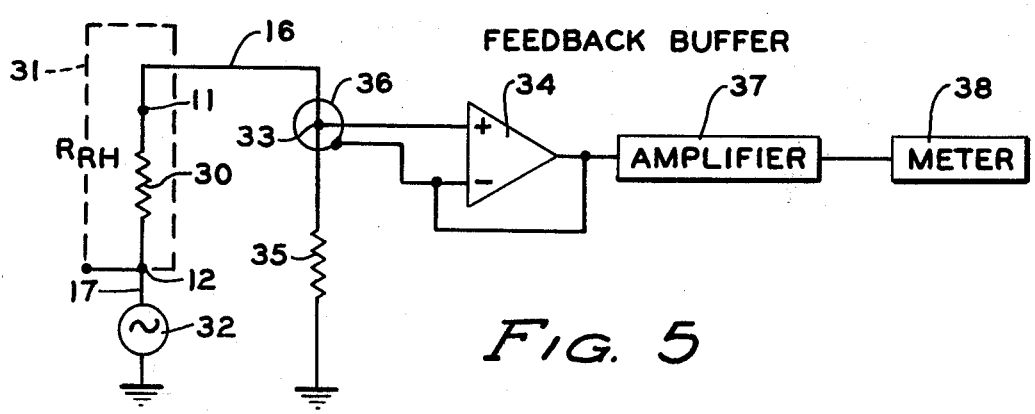
FIG. 5 is an electrical schematic presentation of the high impedance humidity sensor and the related circuit.

Referring now to the schematic circuit of FIG. 5, the relative humidity sensor of FIGS. 1 and 2 is shown as resistive element 30. Element 30, having the generally circular geometry, is effectively bounded at the outer edge of the outer conductive film 12 by a shield 31, here shown in dotted form. The shield is connected to film 12 and conductor 17 in FIG. 5, with conductor 17 being connected to one terminal of an AC generator 32, the other terminal of which at ground. The generator may be, for example, a 1 Hz or a 10 Hz square wave signal of about 1 volt peak-to-peak. The signal need not be square wave. The inner conductive film 11 of the sensor is connected by conductor 16 to a junction 33 and to the positive signal input of a FET (low bias current) OPAMP 34 operating as a feedback buffer. Junction 33 is also connected to a high megohm resistor 35, the other terminal of which is at ground. A guard ring 36 surrounds junction 33, the guard ring being directly connected to the other (negative) input of OPAMP 34. With the feedback circuit around OPAMP 34, there is a zero potential difference between the two inputs whereby guard ring 36 is maintained at the same potential as the signal input to prevent leakage currents. The output of OPAMP 34 is connected to amplifier 37 which controls an indicator such as meter 38.

A low impedance guarding signal can easily be obtained by the use of a "unity gain" feedback amplifier as OPAMP 34. By adding feedback from the output to the inverting (negative) input we have a low impedance signal that tracks or equals the input signal. This low impedance point provides the guarding voltage.

The embodiments of the invention in which an exclusive property or right is claimed are defined as follows:

1. A high impedance relative humidity sensing element comprising:
   a high purity insulating substrate;
   an inner conductive film on the surface of said substrate to form one terminal of said sensing element;
   an outer conductive film on the surface of said substrate, the perimeter of said inner film being completely encompassed by but spaced from said outer film, thereby leaving a continuous loop of substrate exposed between said inner and outer films, said outer film forming the second terminal of the element; and,
   a high impedance humidity responsive film applied to cover said continuous substrate loop and to extend onto said inner and outer conductive films so that said humidity responsive layer forms a continuous loop bridging said spacing in a continuous manner.

2. The sensing element according to claim 1 or 3 wherein the inner and outer conductive films are gold.

3. A circular geometry high impedance relative humidity sensing element comprising:
   a high purity insulating substrate;
   an inner conductive film on the surface of said substrate, said film having a circular perimeter, said film forming one terminal of said sensing element;
   an outer conductive film on the surface of said substrate, the circular perimeter of said inner film being completely encompassed by but spaced from said outer film, the spacing thereby providing a continuous loop of substrate exposed around said inner film, said film forming the other terminal of said element; and,
   a high impedance humidity responsive layer applied to cover said continuous substrate loop and to extend onto said inner and outer films so that said humidity responsive layer forms a continuous loop bridging said layers.

4. A process for producing a high impedance relative humidity sensing element having a generally concentric construction comprising the steps of:
   providing a high purity substrate;
   depositing an inner conductive film on a surface of said substrate, said film having a generally circular perimeter;
   depositing an outer conductive film on the surface of said substrate spaced from but completely encompassing said inner conductive film, the spacing thereby providing a continuous loop of exposed substrate around said inner film;
   depositing a film of high impedance humidity responsive material to cover said continuous substrate loop and to extend onto said inner and outer films so that said humidity responsive layer forms a continuous loop briding said conductive layers.

5. The process according to claim 4 wherein said film of high impedance humidity responsive material is a metal oxide film.

6. The process according to claim 5 and further comprising the step of:
   sintering said deposited metal oxide layer.

7. The process according to claim 4 wherein said inner and outer deposited conductive layers are of gold.

8. The process according to claim 5, wherein the metal oxide is selected from the oxides of the elements contained in Group VIII, Period 4 of the Periodic Table of the Elements.

9. The process according to claim 8 wherein the metal oxide is iron oxide.

10. The sensing element according to claim 1 wherein the substrate is a substantially flat member about 0.025" thick and about 1" across.

11. The sensing element according to claim 2 wherein the gold films are evaporated gold.

12. A high impedance relative humidity indicator comprising:
a high impedance relative humidity sensing element comprising:
an insulating substrate of high-density high-purity ceramic
an inner conductive film on the surface of said substrate to form one terminal of said sensing element;
an outer conductive film on the surface of said substrate, the perimeter of said inner film being completely encompassed by but spaced from said outer film, thereby leaving a continuous loop of ceramic exposed between said inner and outer films, said outer film forming the second terminal of the element; and,
a high impedance humidity responsive film applied to cover said continuous ceramic loop and to extend onto said inner and outer conductive films so that said humidity responsive layer forms a continuous loop bridging said spacing in a continuous manner;
and high impedance circuit means connected to said sensing element comprising:
a source of AC signals connected to said outer film at said second terminal;
a high input impedance OPAMP connected as a feedback buffer having positive and negative signal input electrodes and an output terminal, said output terminal being connected directly to said negative signal input electrode to provide feedback;
connection means from said inner film at said one terminal to the positive input electrode of said OPAMP and also to one terminal of a high megohm resistor, the other terminal of the resistor being at ground;
a guard ring surrounding said connection means, said guard ring being directly connected to said OPAMP negative input electrode whereby the potential at said guard ring is controlled by said feedback buffer OPAMP to be at the same potential as that at said positive signal input electrode so that leakage current is prevented from said connection means; and
means comprising indicator means connected to said OPAMP output terminal.

13. A sensing element according to claims 1, 3 or 12 wherein the high purity insulating substrate is selected from a group consisting of alumina, AlSiMag, or quartz.

14. The indicator according to claim 12 wherein the high input impedance OPAMP is a unity gain amplifier.

15. The humidity sensing element according to claims 1, 3 or 12 wherein the humidity responsive film is a metal oxide.

16. The humidity sensing element according to claim 15 wherein the metal oxide is selected from the oxides of the elements contained in Group VIII, Period 4 of the Periodic Table of the Elements.

17. The humidity sensing element according to claim 16 wherein said metal oxide is iron oxide.

18. The humidity sensing element according to claim 17 wherein said iron oxide is $Fe_2O_3$.

19. The humidity sensing element according to claims 1, 3 or 12 wherein the humidity responsive film is a hygroscopic polymer.

20. The humidity sensing element according to claim 19 wherein the hydroscopic polymer is polyvinyl alcohol with lithium chloride.

21. The humidity sensing element according to claim 19 wherein the hydroscopic polymer is polyethelene fluoride.

22. The humidity sensing element according to claims 1, 3 or 12 wherein the humidity responsive film is an inorganic salt selected from a group consisting of sodium hydrogen phosphate, lead iodide, cerium titanate and lithium fluoride.

* * * * *